US00PP37288P3

(12) United States Plant Patent
Danziger

(10) Patent No.: US PP37,288 P3
(45) Date of Patent: Feb. 24, 2026

(54) ***SCAEVOLA* PLANT NAMED 'DSCAPW1335'**

(50) Latin Name: *Scaevola aemula*
Varietal Denomination: DSCAPW1335

(71) Applicant: Gavriel Danziger, Moshav Mishmar Hashiva (IL)

(72) Inventor: Gavriel Danziger, Moshav Mishmar Hashiva (IL)

(73) Assignee: DANZIGER "DAN" FLOWER FARM, Beit Dagan (IL)

( * ) Notice: Subject to any disclaimer, the term of this patent is extended or adjusted under 35 U.S.C. 154(b) by 0 days.

(21) Appl. No.: 18/905,111

(22) Filed: Oct. 2, 2024

(65) Prior Publication Data

US 2025/0113747 P1 Apr. 3, 2025

Related U.S. Application Data

(60) Provisional application No. 63/542,199, filed on Oct. 3, 2023.

(51) Int. Cl.

| | |
|---|---|
| ***A01H 5/02*** | (2018.01) |
| ***A01H 6/00*** | (2018.01) |
| ***A01H 6/14*** | (2018.01) |

(52) U.S. Cl.
USPC ..... Plt./363
CPC ..... *A01H 6/14* (2018.05)

(58) Field of Classification Search
USPC ..... Plt./263.1, 363
See application file for complete search history.

(56) References Cited

U.S. PATENT DOCUMENTS

PP21,443 P2 * 11/2010 Courtney ..... A01H 5/02
Plt./363

OTHER PUBLICATIONS

Grabowski. 2015. Evaluation of Annual Bedding Plants for Resistance to White Mold. HortScience 50: 259-262. (Year: 2015).*

Proven Winner website. 2025. https://www.provenwinners.com/plants/scaevola/whirlwind-white-fan-flower-scaevola-aemula-0. 3 pages. (Year: 2025).*

* cited by examiner

*Primary Examiner* — Karen M Redden
(74) *Attorney, Agent, or Firm* — C. Anne Whealy

(57) ABSTRACT

A new and distinct cultivar of *Scaevola* plant named 'DSCAPW1335', characterized by its upright to outwardly spreading and mounding to eventually trailing plant habit; freely branching habit, dense and bushy habit; moderately vigorous to vigorous growth habit; relatively narrow and medium green-colored leaves; freely flowering habit; relatively large pure white-colored flowers; and good garden performance.

2 Drawing Sheets

CROSS-REFERENCED TO CLOSELY-RELATED APPLICATIONS

Figure 1:
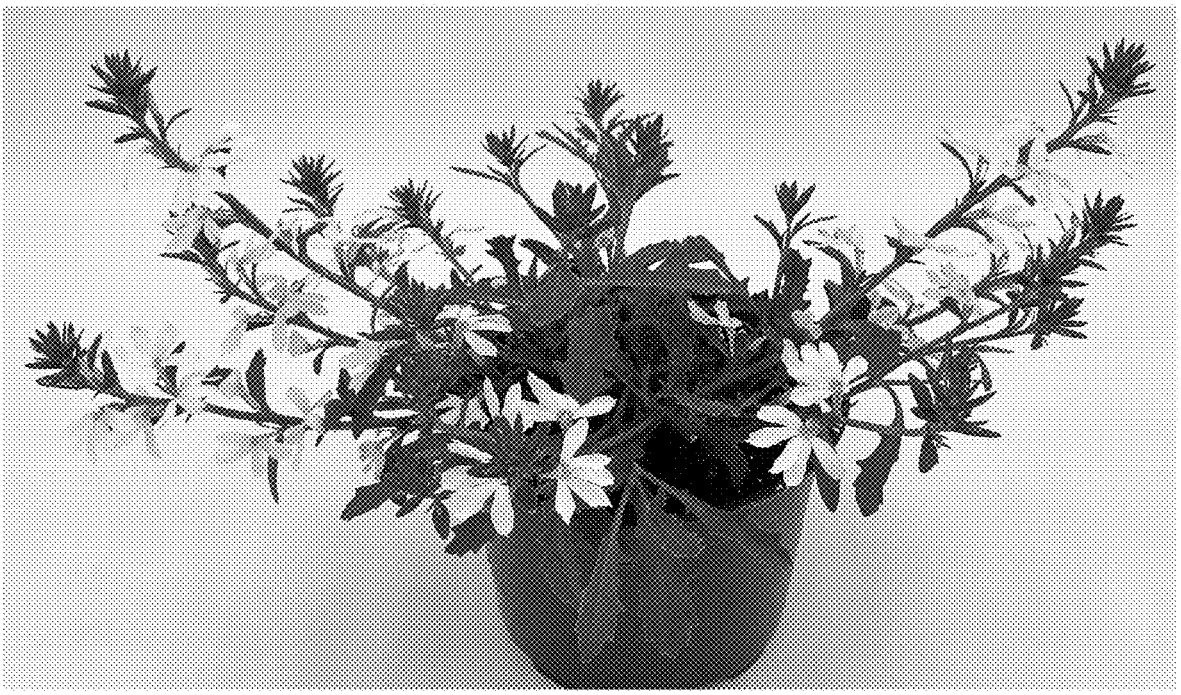

Title: *Scaevola* Plant Named 'DSCAPW1335'
Inventor: Gavriel Danziger
Filed: Oct. 3, 2023
Ser. No. 63/542,199
Inventor/Applicant hereby claims the benefit of this provisional U.S. Patent Application.
Botanical designation: *Scaevola aemula.*
Cultivar denomination: 'DSCAPW1335'.

BACKGROUND OF THE INVENTION

The present invention relates to a new and distinct cultivar of *Scaevola* plant, botanically known as *Scaevola aemula* and hereinafter referred to by the name 'DSCAPW1335'.

The new *Scaevola* plant is a product of a planned breeding program conducted by the Inventor in Moshav Mishmar Hashiva, Israel. The objective of the breeding program is to create new compact and freely-branching *Scaevola* plants with numerous attractive flowers and good garden performance.

The new *Scaevola* plant originated from a self-pollination made by the Inventor in 2015 in Moshav Mishmar Hashiva, Israel of a proprietary selection of *Scaevola aemula* identified as code number SC-15-1176, not patented. The new *Scaevola* plant was discovered and selected by the Inventor as a single flowering plant from within the progeny of the stated self-pollination in a controlled greenhouse environment in Moshav Mishmar Hashiva, Israel on Nov. 21, 2016.

Asexual reproduction of the new *Scaevola* plant by vegetative terminal cuttings in a controlled greenhouse environment in Moshav Mishmar Hashiva, Israel since Nov. 21, 2016 has shown that the unique features of this new *Scaevola* plant are stable and reproduced true to type in successive generations.

SUMMARY OF THE INVENTION

Plants of the new *Scaevola* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'DSCAPW1335'. These characteristics in combination distinguish 'DSCAPW1335' as a new and distinct *Scaevola* plant:

1. Upright to outwardly spreading and mounding to eventually trailing plant habit.
2. Freely branching habit, dense and bushy habit.
3. Moderately vigorous to vigorous growth habit.
4. Relatively narrow and medium green-colored leaves.
5. Freely flowering habit.
6. Relatively large pure white-colored flowers.
7. Good garden performance.

Plants of the new *Scaevola* can be compared to plants of the parent selection. Plants of the new *Scaevola* differ primarily from plants of the parent selection in the following characteristics:

1. Plants of the new *Scaevola* have narrower and lighter green-colored leaves than plants of the parent selection.
2. Plants of the new *Scaevola* have larger flowers than plants of the parent selection.

Plants of the new *Scaevola* can be compared to plants of the *Scaevola aemula* 'White Touch', not patented. In side-by-side comparisons, plants of the new *Scaevola* differ from plants of the 'White Touch' in the following characteristics:

1. Plants of the new *Scaevola* are more trailing than and not as mounding as plants of 'White Touch'.
2. Plants of the new *Scaevola* have narrower leaves than plants of 'White Touch'.
3. Plants of the new *Scaevola* have larger flowers than plants of 'White Touch'.

Plants of the new *Scaevola* can also be compared to plants of the *Scaevola aemula* 'DSCAVPUHAZ', disclosed in U.S. Plant Pat. No. 29,544. In side-by-side comparisons, plants of the new *Scaevola* differ from plants of the 'DSCAVPUHAZ' in the following characteristics:

1. Plants of the new *Scaevola* are more trailing than and not as upright as plants of 'DSCAVPUHAZ'.
2. Plants of the new *Scaevola* have larger flowers than plants of 'DSCAVPUHAZ'.
3. Plants of the new *Scaevola* have white-colored flowers whereas plants of 'DSCAVPUHAZ' have dark purple-colored flowers.

BRIEF DESCRIPTION OF THE PHOTOGRAPHS

The accompanying colored photographs illustrate the overall appearance of the new *Scaevola* plant showing the colors as true as it is reasonably possible to obtain in colored reproductions of this type. Colors in the photographs may differ slightly from the color values cited in the detailed botanical description which accurately describe the colors of the new *Scaevola* plant.

The photograph on the first sheet (FIG. 1) is a side perspective view of a typical flowering plant of 'DSCAPW1335' grown in a container.

Figure 2:
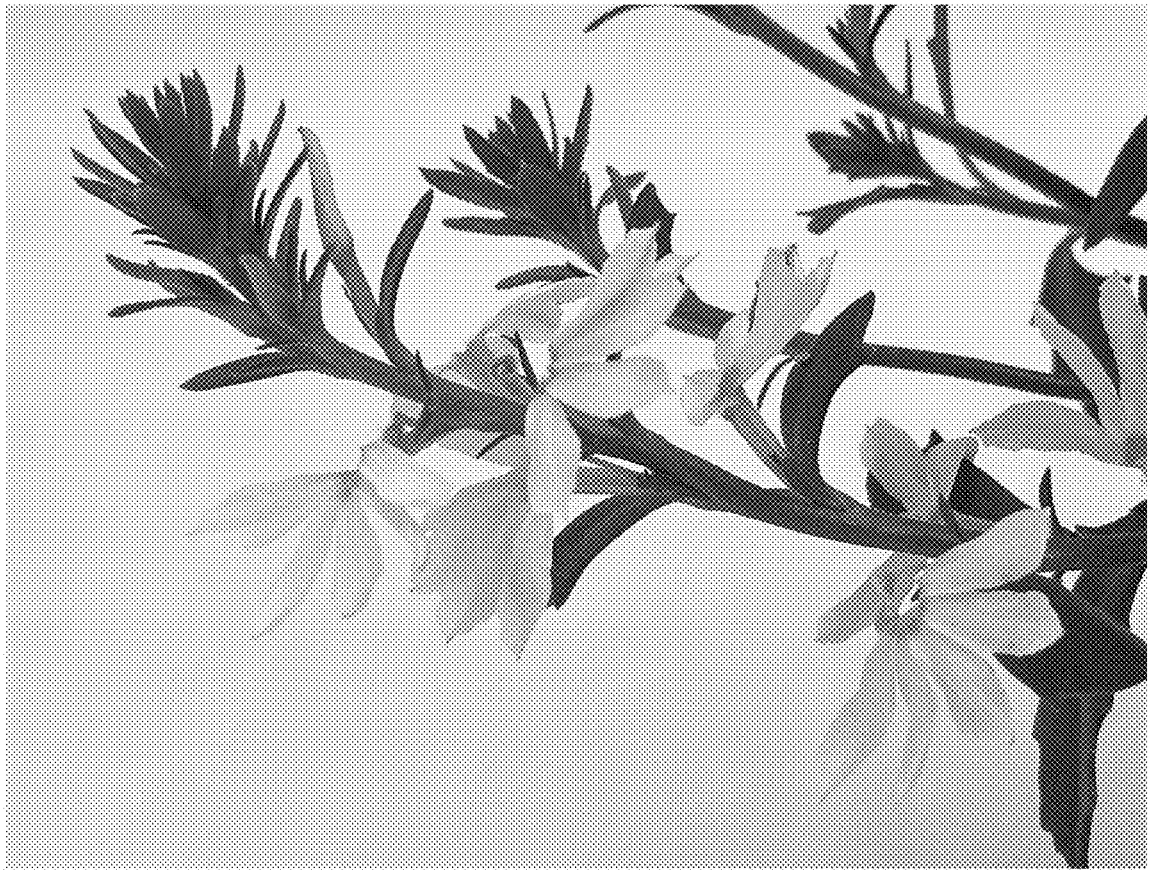

The photograph on the second sheet (FIG. 2) is a close-up view of a typical flowering plant of 'DSCAPW1335'.

DETAILED BOTANICAL DESCRIPTION

The aforementioned photographs and following observations and measurements describe plants grown during the late summer to early autumn in 813 ml containers in a glass-covered greenhouse in Loudon, New Hampshire and under cultural practices typical of commercial *Scaevola* production. During the production of the plants, day temperatures ranged from 18° C. to 20° C. and night temperatures ranged from 16° C. to 18° C. Plants were pinched one time and were eight weeks from planting rooted young plants when the photographs and description were taken. In the following description, color references are made to The Royal Horticultural Society Colour Chart, 2015 Edition, except where general terms of ordinary dictionary significance are used.

Botanical classification: *Scaevola aemula* 'DSCAPW1335'.

Parentage:

*Female, or seed, parent.*—Proprietary selection of *Scaevola aemula* identified as code number SC-15-1176, not patented.

*Male or pollen parent.*—Proprietary selection of *Scaevola aemula* identified as code number SC-15-1176, not patented.

Propagation:

*Type.*—By vegetative tip cuttings.

*Time to initiate roots, summer.*—About two to three weeks at temperatures about 25° C. to 35° C.

*Time to initiate roots, winter.*—About 21 to 30 days at temperatures about 7° C. to 18° C.

*Time to produce a rooted young plant, summer.*—About four weeks at temperatures about 25° C. to 35° C.

*Time to produce a rooted young plants, winter.*—About 45 days at temperatures about 7° C. to 18° C.

*Root description.*—Fibrous, fine; typically white in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Upright to outwardly spreading and mounding to eventually trailing plant habit; moderately vigorous to vigorous growth habit and moderate growth rate.

*Branching habit.*—Freely branching habit with lateral branches potentially forming at every node; pinching enhances branching potential.

*Plant height.*—About 19 cm to 21 cm.

*Plant diameter* (*area of spread*).—About 33 cm to 35 cm.

Lateral branch description:

*Length.*—About 22 cm to 25 cm.

*Diameter.*—About 4 mm to 5 mm.

*Internode length.*—About 1.2 cm to 1.75 cm.

*Aspect.*—Upright to outwardly to eventually trailing.

*Texture.*—Moderately pubescent; slightly rough.

*Color.*—Close to 146A.

Leaf description:

*Arrangement.*—Alternate, simple.

*Length.*—About 6 cm to 6.5 cm.

*Width.*—About 2 cm to 2.5 cm.

*Shape.*—Narrowly spatulate.

*Apex.*—Mucronate.

*Base.*—Attenuate.

*Margin.*—Broadly serrate; sinuses divergent and shallow to medium in depth.

*Texture, upper and lower surfaces.*—Smooth, glabrous; rough, coriaceous.

*Venation pattern.*—Pinnate, reticulate.

*Color*.—Developing and fully expanded leaves, upper surface: Close to 146A; venation, close to 146A. Developing and fully expanded leaves, lower surface: Close to 146B; midvein, close to 144A and lateral venation, close to 146B.

*Petioles*.—Length: About 2.25 cm. Width: About 3 mm. Texture: Smooth, glabrous. Color, upper and lower surfaces: Close to 146A.

Flower description:

*Flower type and shape*.—Zygomorphic, semi-circular, fan-shaped flowers with five petals fused at the base to form a tubular flower throat; flower throat open along the upper surface exposing the reproductive organs.

*Flower arrangement and quantity*.—Solitary sessile flowers arising from upper leaf axils; flowers mostly horizontal; freely flowering habit with typically about 12 to 20 flowers per lateral branch and about 240 to 500 flowers developing per plant during the flowering season.

*Flowering time*.—Plants begin flowering after about five to seven weeks after planting rooted young plants; long flower period, plants flower continuously from spring into the autumn in New Hampshire.

*Flower longevity*.—Depending on temperature, flowers typically last about seven to ten days on the plant; flowers not persistent.

*Fragrance*.—None detected.

*Flower buds*.—Length: About 1 cm. Diameter: About 2.5 mm to 4 mm. Shape: Narrow conical, tapering. Color: Close to 144A.

*Flowers*.—Diameter: About 2.75 cm to 3 cm. Depth: About 2.5 cm to 2.75 cm. Throat diameter: About 5 mm. Tube length: About 1.1 cm to 1.4 cm. Tube diameter, distally: About 5.5 mm. Tube diameter, proximally: About 3.5 mm.

*Petals*.—Quantity per flower: Five, fused at base. Length, beyond tube: About 1.5 cm. Width, beyond tube: About 5 mm to 5.5 mm. Shape: Oblanceolate. Apex: Cuspidate to mucronate. Margin: Entire; not undulate. Texture, upper and lower surfaces: Smooth, glabrous. Texture, throat: Smooth, glabrous. Texture, tube: Smooth, glabrous. Color: When opening, upper and lower surfaces: Close to NN155D. Fully opened, upper and lower surfaces: Close to NN155D; venation, similar to lamina colors; color does not change with subsequent development. Throat: Close to 1A; venation, close to 1A. Tube: Close to 154C; venation, close to 154C.

*Sepals*.—Quantity per flower: Three, two smaller with a larger central sepal. Length: Smaller sepals, about 1 cm; larger sepal, about 2 cm. Width: Smaller sepals, about 1 mm; larger sepal, about 5 mm. Shape: Linear. Apex: Acute. Base: Fused. Margin: Entire. Texture, upper surface: Slightly pubescent. Texture, lower surface: Smooth, glabrous. Color, upper surface: Close to 137A. Color, lower surface: Close to 137B.

*Reproductive organs*.—Androecium: Stamen quantity per flower: Five. Filament length: About 3 mm to 5 mm. Filament color: Close to NN155D. Anther length: About 1.25 mm. Anther shape: Narrowly oblong. Anther color: Close to 10A. Pollen: None observed. Gynoecium: Pistil quantity per flower: One. Pistil length: About 1.5 cm. Style color: Close to 1 cm. Stigma color: Close to 154D. Ovary color: Close to 144A.

*Seeds and fruits*.—To date, seed and fruit development have not been observed on plants of the new *Scaevola*.

Garden performance: Plants of the new *Scaevola* have been observed to have good garden performance and to tolerate rain, wind and temperatures ranging from about 10° C. to about 35° C.

Pathogen & pest resistance: To date, plants of the new *Scaevola* have not been shown to be resistant to pathogens and pests common to *Scaevola* plants.

It is claimed:

1. A new and distinct *Scaevola* plant named 'DSCAPW1335' as herein illustrated and described.

* * * * *